United States Patent [19]

Underwood et al.

[11] Patent Number: 5,270,067
[45] Date of Patent: Dec. 14, 1993

[54] IMPREGNATED CASING AND METHOD OF MAKING THE SAME

[75] Inventors: Gary L. Underwood, Manitowoc, Wis.; Jose I. Recalde, Pamplona, Spain

[73] Assignee: Red Arrow Products Company Inc., Manitowoc, Wis.

[21] Appl. No.: 743,867

[22] Filed: Aug. 12, 1991

Related U.S. Application Data

[60] Continuation-in-part of Ser. No. 416,963, Oct. 4, 1989, Pat. No. 5,039,537, which is a continuation-in-part of Ser. No. 343,928, Apr. 26, 1989, Pat. No. 4,959,232, and Ser. No. 358,650, May 26, 1989, Pat. No. 4,994,297, which is a division of Ser. No. 119,673, Nov. 12, 1987, Pat. No. 4,876,108.

[51] Int. Cl.$^5$ .................. A23L 1/317; A23L 1/232
[52] U.S. Cl. ................... 426/138; 426/140; 426/315; 426/533
[58] Field of Search ............ 426/138, 140, 533, 315

[56] References Cited

U.S. PATENT DOCUMENTS

| | | | |
|---|---|---|---|
| 3,106,473 | 10/1963 | Hollenbeck | 99/229 |
| 3,330,669 | 7/1967 | Hollenbeck | 99/166 |
| 4,431,032 | 2/1984 | Nicholson | 138/118 |
| 4,431,033 | 2/1984 | Nicholson | 138/118 |
| 4,496,595 | 1/1985 | Nicholson | 426/284 |
| 4,504,500 | 3/1985 | Schneck et al. | 426/265 |
| 4,504,501 | 3/1985 | Nicholson | 426/284 |
| 4,504,507 | 3/1985 | Nicholson | 426/533 |
| 4,505,939 | 3/1985 | Chiu | 426/135 |
| 4,511,613 | 3/1985 | Nicholson et al. | 428/36 |
| 4,525,397 | 6/1985 | Chiu | 428/36 |
| 4,540,613 | 9/1985 | Nicholson et al. | 428/36 |
| 4,657,765 | 4/1987 | Nicholson et al. | 426/250 |
| 4,717,576 | 1/1988 | Nicholson et al. | 426/533 |
| 4,818,551 | 4/1989 | Stall et al. | 426/420 |
| 4,876,108 | 10/1989 | Underwood et al. | 426/650 |
| 4,959,232 | 9/1990 | Underwood | 426/271 |
| 4,994,297 | 2/1991 | Underwood et al. | 426/650 |
| 5,039,537 | 8/1991 | Underwood | 426/271 |
| 5,135,770 | 8/1992 | Underwood | 426/315 |

*Primary Examiner*—Carolyn Paden
*Attorney, Agent, or Firm*—Marshall, O'Toole, Gerstein, Murray & Borun

[57] ABSTRACT

The present invention relates to a casing which is impregnated with a high browning, low flavor liquid composition in order to impart a desirable brown color to a food contained in the casing without adding undesirable sensory characteristics to the food.

21 Claims, 1 Drawing Sheet

IMPREGNATED CASING AND METHOD OF MAKING THE SAME

CROSS REFERENCE TO RELATED APPLICATIONS

This invention is a continuation-in-part of U.S. Pat. application Ser. No. 07/416,963 filed Oct. 4, 1989, now U.S. Pat. No. 5,039,537 which is a continuation-in-part application of Ser. No. 07/343,928, filed Apr. 26, 1989, now U.S. Pat. No. 4,959,232 and Ser. No. 07/358,650, filed May 26, 1989, now U.S. Pat. No. 4,994,297 which is a divisional application of Ser. No. 07/119,673 now U.S. Pat. No. 4,876,108.

FIELD OF THE INVENTION

The present invention relates generally to a casing impregnated with a high browning, low flavor liquid composition that imparts or adds a desirable brown, smoked color to an encased food. More particularly, the casing is impregnated with a liquid composition that browns an encased food but does not add a strong, smoked flavor to the food. A method of making impregnated casings is also within the scope of this invention.

BACKGROUND OF THE INVENTION

Using liquid solutions (often referred to as liquid smoke) as a replacement for conventionally smoking foods by direct contact with wood smoke has become a standard industry practice. One known liquid smoke solution for flavoring and coloring foods is an aqueous liquid smoke flavoring described by Hollenbeck in U.S. Pat. No. 3,106,473. Another useful solution for flavoring and coloring foods is obtained from a process for isolating the organic components of the fast pyrolysis of wood or cellulose described by Underwood et al. in U.S. Pat. No. 4,876,108. When such liquid solutions are applied to the surface of meats and other protein-containing foods, organic components in the solution give a food a characteristic smoke flavor and react with the proteins of the food to give a brown, smoked color typical of a conventionally smoked food.

Surface appearance and flavor are important factors in the commercial and consumer acceptance of "liquid smoked" foods. A common feature of most varieties of such foods involves using various types of liquid solutions of wood-derived smoke constituents for imparting both characteristic flavor and color to the food.

The application of a liquid smoke solution to a food is generally carried out in a variety of ways including: spraying or dipping a food during processing, incorporating the liquid smoke in the recipe itself, or treating a casing which contacts a food during processing. The conventional operations of spraying or dipping a casing have not been completely satisfactory due to an inability to treat or coat the encased food uniformly. In addition, treating a casing with a liquid smoke solution does not always provide a food having the desired surface appearance. For example, when a liquid smoke solution is applied to a meat the processor normally must give up browning in order to keep the flavor at a desired level because the flavor imparting ability of known liquid smoke solutions is generally too intense at a desired brown color.

In addition, encased sausages treated by application of a conventional liquid smoke to a casing during processing have been found to yield (after peeling the casing from the sausage), sausages that are lacking in smoke color and that have poor color uniformity between sausages and batches of sausages. In addition to lack of uniformity of coloration when casings are treated with conventional liquid solutions, the surface of a treated sausage often may include light and dark streaks, light and dark blotches, uncolored spots or specks appearing at the ends of the sausage, dark surface discolorations or black spots appearing on the casing or on the sausage.

Furthermore, applying a liquid smoke to encased food products, such as by spraying or dipping, also causes unwanted pollution and equipment corrosion problems for the food processor.

It has also been reported that when a cellulosic casing, made from either fibrous or nonfibrous gel stock casing, is treated with a known highly acidic (pH of about 2.0 to 2.5), tar-containing, aqueous liquid smoke, tarry deposits accumulate on coating and squeeze rollers of conventional coating apparatus. These deposits cause the casing to stick to the rollers and eventually force a shutdown of the coating apparatus.

One reported method to minimize some of these problems associated with imparting smoke color and flavor to foods uses a "tar-depleted" liquid smoke solution to coat the surface of a casing. For example, unwanted tars may be partially removed from conventional liquid smoke by neutralizing the liquid smoke with base to precipitate the tars. Use of such a neutralized, tar-depleted liquid smoke to treat a casing helps to prevent the tarry deposit accumulation problem. Unfortunately, the neutralizing method for forming a tar-depleted liquid smoke is not satisfactory. Tar-depleted liquid smoke solutions have a strong flavor but do not have a sufficient coloring ability because the coloring ability of a liquid smoke solution is typically known to decline with increasing pH. Further, the viscosity of a liquid smoke solution increases substantially when the solution is neutralized especially after concentration. These factors limit most applications, particularly where a high coloring ability is desired.

Similarly, a solvent extraction process may be employed to make tar-depleted liquid smoke. Such a process is reported in U.S. Pat. Nos. 4,505,939, 4,431,032, 4,431,033, 4,496,595, 4,525,397, 4,504,501, 4,504,507, 4,657,765 and 4,717,576. In this process, a tar-containing liquid smoke solution is extracted with a nonreactive or reactive organic solvent which is immiscible in the liquid smoke solution under conditions sufficient to form a tar-enriched solvent fraction and a tar-depleted liquid smoke fraction. Using this solvent extraction method, it is possible to make a tar-depleted liquid smoke solution capable of imparting smoke color, odor, and flavor to foods.

The tar-depleted liquid smoke solution made from the solvent extraction process, unless it is neutralized, is generally still highly acidic, and thus may degrade or interfere with the integrity of cellulosic casings. If a tar-depleted liquid smoke solution is partially neutralized, the coloring ability also typically declines with increasing pH without a corresponding decline in flavor. Thus, satisfactory coloring with extracted liquid smoke solutions requires adding a solution having too much flavoring capability. Similarly, if enough of a tar-depleted liquid smoke solution is added to a casing to impart satisfactory color, the amount of organic components in the casing becomes to great. These overloaded casings may become rubber-like and cannot be handled or shirred. In addition, the process of adding large amounts of a tar. depleted liquid smoke solution to casings is very difficult using conventional techniques. Although tar-depleted liquid smoke solutions address some of the problems of using these solutions to color encased foods, the undesirable sensory aspects have been a factor for the lack of commercial acceptance of these products. There is a need in the industry for impregnated casings having both good coloring or browning properties and acceptable flavoring properties.

SUMMARY OF THE INVENTION

The present invention provides a casing suitable to impart a brown color to food and provides a method of making a casing that includes contacting a casing with a high browning, low flavor liquid composition having a high ratio of browning index to the amount of soluble organic components in the composition (° Brix).

The ratio of browning index to the organic components is preferably selected to give a liquid composition that imparts a satisfactory brown, smoked color to a food contained in the casing without adding undesired sensory properties to the food. A preferred ratio of browning index to ° Brix is 0.9, and a more preferred ratio is 1.5.

For specific organic components in the liquid composition, a preferred ratio of browning index to organic acids or salts thereof is greater than 5.0, and a more preferred ratio is greater than 12.0. A preferred ratio of browning index to carbonyls is greater than 1.8, and a more preferred ratio is greater than or equal to 2.0. A preferred ratio of browning index to phenols is greater 8.5, and a more preferred ratio is greater than 30.0.

In addition, the viscosity of a preferred liquid composition, whether or not the solution is pH adjusted, is less than 300 cps, preferably less then 90 cps, and more preferably less than 10 cps.

Cellulosic casings of the invention, both nonreinforced cellulosic casings and fibrous reinforced cellulosic casings, impregnated with a high browning, low flavor liquid composition have a low ratio of organic components to browning index density, as defined below. A preferred ratio of organic components to browning index density is less than 12.0, and a more preferred ratio of organic components to browning index is less than 5.0.

Cellulosic casings impregnated with a high browning, low flavor liquid composition also have a low ratio of phenols to browning index density, a preferred ratio of phenols to browning index density is less than 0.1.

Furthermore, cellulosic casings impregnated with a high browning, low flavor liquid composition have a browning index density greater than 0.08 and preferably the browning index density is in the range of 0.08 to 3.4.

DETAILED DESCRIPTION

Figure 1:
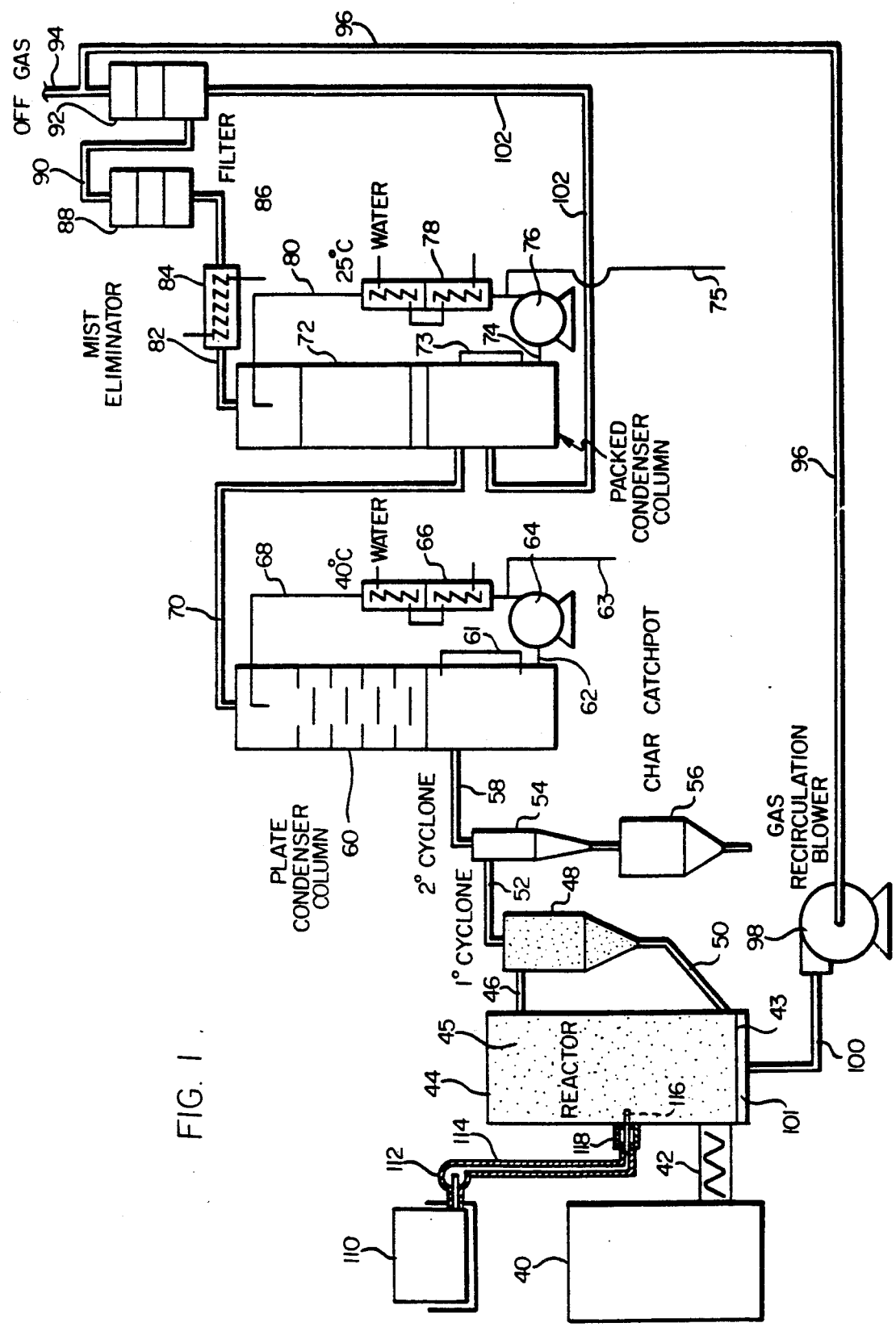
FIG. 1 illustrates a fast pyrolysis apparatus.

The present invention provides a casing and a method of making a casing in which the casing has higher browning capabilities and less intense flavor properties compared to previously reported food casings.

As used herein the term "organic components" means components of a liquid composition, different than water, which are included in browning or liquid compositions suitable for application to a casing. Salts derived from neutralizing organic acids are included in this term as well as any inorganic components (although these inorganic components are, for practical purpose, very insignificant). The total percentage of organic components or total organics for a liquid composition are determined using the formula:

100 − (water content determined by the Karl Fisher titration method).

The term "acids" means the total amount of organic acids plus alkaline salts produced during their neutralization and is a subgroup of the components included within the meaning of organic components.

The term "Browning Index Density" (BID) is a measure of the browning ability of a casing per unit of area that is calculated by multiplying the following values: the amount of organic components added to the casing or organics load (ORGANICS IN CASING measured as mg/cm$^2$); 100 divided by the percent of organic components in the added liquid (100/% ORGANICS IN LIQUID); and the browning index of the liquid composition divided by 1000 (Browning Index/1000). Thus, BID values are determined using the formula:

(ORGANICS IN CASING) (100/% ORGANICS IN LIQUID) (BROWNING INDEX)/1000).

The amount of organic components which are added to a casing is calculated using the formula:

(TOTAL WEIGHT) − (WATER) − (GLYCOL) (CELLULOSE)

Casings suitable for use in the present invention include tubular casings, and preferably tubular cellulosic casings, that are prepared by any of the methods that are well known in the art.

In earlier attempts to produce liquid smoke-containing cellulose casings, the only way to get acceptable coloring properties for the casings required loading the casings with substantial amounts of organic components (carbonyls, phenols, acids and salts thereof) derived from various liquid smoke solutions. Detrimentally, substantial portions of these solutions contained unnecessary organic components that had no beneficial properties or that even imparted unsuitable sensory properties to foods. Furthermore, very high amounts of organic components were needed on cellulose casings in order to give a satisfactory product. This overloading also detrimentally affected both the physical characteristics of the casings and the processes which were used to apply the solutions to the casings. Thus, the present invention provides a casing containing a minimum casing load of desired organic components from a desired liquid composition.

In the past, the liquid smoke solutions that were typically applied to casings were most often obtained from products having high acid content and included acids that were difficult or impossible to remove and that had to be neutralized before these solutions were applied to cellulosic casings. When these conventional solutions were neutralized, however, the solutions eventually contained too many acid derived salts and the solutions became too viscous to be readily applied to casings in an easy straight forward way. Solutions which were too viscous also overloaded casings with undesired and unnecessary organic components.

Practical processing conditions have established that low viscosity solutions are highly desirable when liquid compositions have to be applied to casings in order to impregnate them with adequate levels of coloring or browning components. If high viscosity compositions are used, they may also give an uneven distribution of organic components on casings because the application process becomes difficult. In addition, the absorption of high viscosity solutions into casings is slow and high speed coating methods cannot be used. Furthermore, in high viscosity solutions, organic components do not move freely in solution and diffusion processes of the solutions into casings are slow, making the impregnation process more difficult.

The advantages of the cellulosic casings of the invention are due, in part, to three characteristics of the liquid compositions which are applied to the casings. Preferred liquid compositions have:

i) low acid content (the ratio of browning index to total organic components is very high);

ii) high levels of browning carbonyls (the ratio of browning index to carbonyls is higher than in reported liquid smoke solutions and results in food products having good coloring using casings treated with less solution); and iii) low levels of phenols (the high ratio of browning index to phenols gives a food with desirable brown color and less flavor).

Two types of cellulosic casings, nonfibrous and fibrous, are within the scope of the invention. Such casings are either non-fibrous, flexible, thin-walled seamless casings formed of regenerated cellulose or cellulosic casings having a fibrous reinforcing web embedded in the wall of the casings.

Any well known method may be used to contact suitable casings with a desired liquid composition. See, for example, the methods disclosed in U.S. Pat. Nos. 3,330,669 and 4,504,500. Suitable methods for contacting casings with a liquid composition are also described in U.S. Pat. application Ser. No. 07/416,963 filed Oct. 4, 1989, which is incorporated herein by reference.

A liquid composition may be externally applied to a casing by passing the casing through a bath of the liquid composition. The liquid composition is generally allowed to soak into the casing for an amount of time sufficient for the casing to incorporate the desired amount of organic components into the casing before doctoring off any excess liquid, typically by passing the casing through squeeze rollers or wipers. The liquid composition may also be externally applied to the casing by methods other than dipping, such as spraying, brushing or roll-coating. In these types of applications, low viscosity liquid compositions are preferred.

Another method of treating a casing with a liquid composition of this invention involves passing a flattened, tubular, cellulosic casing over guide rolls through a dip tank which contains the liquid composition. The casing passes over additional guide rolls after exiting the dip tank, and then passes between squeeze rollers which minimize any excess carryover of the liquid composition. The total contact time of the casing with the liquid composition in the dip tank, and with excess liquid composition on the casing passing over the guide rolls before the casing passes through the squeeze rollers, relates to the amount of organic components incorporated into the casing.

After contact with the liquid composition the externally treated casing is then sent on to further conventional processing, including conventional humidification, as may be required, and conventional shirring.

Alternatively, the liquid composition may be applied to the internal surface of a casing by any of several well-known procedures. These procedures include slugging or bubble coating, spraying, and coating while shirring. The slugging method for coating the inside of a casing involves filling a portion of the casing with the liquid composition, so that a slug of the composition generally resides at the bottom of a "U" shape formed by the casing. A continuous indefinite length of casing, keeping the slug confined within the casing, then moves past the slug and is coated on its inside wall by the liquid composition contained within the slug.

Both externally or internally impregnated casings may be shirred by conventional methods or, before shirring, they may be dried or humidified to a water content suitable for shirring or further processing. The need for conventional drying or humidification after treatment with the composition depends on the water content of the casing after treatment and the type of casing. If the casing is a nonfibrous casing, a water content within the range of about 8-18 wt. % water immediately before shirring is typical, and for a fibrous casing a water content within the range of about 11-35 wt. % water immediately before shirring is typical, where weight percent is based on the total weight of casing including water.

In the indirect application of the liquid composition to a food from a casing, the lack of a strong or an undesirable flavor is a notable, additional advantage. Conventional or known liquid smoke solutions such as tar-depleted liquid smoke solutions generally must be used at high concentrations to impart enough color or browning to an encased food. These high concentrations, however, typically have a flavor which may be more intense than desired. The use of the liquid compositions provided hereby on casings allows a processor to achieve a desired brown, smoke. like color without necessarily imparting too much flavor to a food.

It is to be noted that the liquid composition which is impregnated in the casing, whether externally or internally applied, does not exist solely as a surface coating. Color and flavor components of the liquid composition which are coated on a casing penetrate the cellulosic structure of the casing as the cellulose absorbs the moisture of the composition.

To obtain a suitable liquid composition, a fast pyrolysis process which uses hot particulate solids and/or inert gases to rapidly transfer heat to the wood feedstock in a reactor system is preferred. This process uses short vapor residence times (depending upon the reactor conditions) and results in very high gas or liquid yields from biomass. Char yields are from 0-15% depending upon the feedstock and reactor temperature. Maximum gas yields may be about 90% of the feedstock mass at 900° C. and maximum liquid yields may be about 85% of the feedstock mass at 600-650° C. A suitable apparatus for this process is described in U.S. Pat. No. 4,876,108 and the related divisional U.S. Pat. No. 4,994,297. This type of apparatus can be operated at temperatures between 350°-1000° C. with vapor residence times between 0.03-3 seconds.

FIG. 1 illustrates an apparatus useful for the fast pyrolysis of a suitable feedstock by a rapid thermal process. Bin (40) stores a supply of the feedstock such as wood, cellulose, sugars, or polysaacharides in granular or powder form. The feedstock is removed from the bin (40) by an auger (42) and fed to the lower interior portion of the reactor (44) above a windbox (101) and a gird plate (43). The auger (42) may be water cooled at the inlet to the reactor to prevent premature pyrolysis, which can produce tarry materials. Alternatively, a solution or syrup of a carbohydrate-containing liquid feedstock may be injected into the reactor using a suitable well known injector apparatus. A heated storage tank (110) stores a supply of a liquid feedstock. The liquid feedstock is pumped from the storage tank (110) by a pump (112) through a clean jacketed conduit (114). The liquid feedstock enters the reactor (44) through an injector nozzle (116). The injector nozzle (116) may be cooled at the inlet in the reactor by a water-cooled jacket (118) to prevent premature pyrolysis of the liquid feedstock in the injector nozzle.

A stream of recirculation gas transport fluid is fed by a conduit (100) into the windbox (101), through the grid plate (43) and into the lower portion of the reactor (44) containing a heat transfer medium such as sand (45). Rapid mixing and conductive heat transfer from the sand (45) to the sugar or starch feedstock occurs in the reactor (44). Pyrolytic conversion of the feedstock to a raw product vapor is initiated and continues through the reactor with upward flow into the primary cyclone separator (48). The pyrolysis stream comprising sand (45) and pyrolysis vapor is removed from the reactor (44) by conduit (46) and fed to primary cyclone separator (48). The hot sand (45) is removed from the product vapor stream in the separator (48) and recycled by means of a conduit (50) to the reactor (44). The recycled sand (45) is reintroduced into the lower portion of the reactor (44) at a point above the grid plate (43). Product vapor containing char is withdrawn from the primary cyclone separator (48) by a conduit (52) and fed to a secondary cyclone separator (54) which can be a high efficiency reverse flow cyclone separator. Char and solid sand fines are removed in the secondary cyclone and fed therefrom to a char catchpot (56) for disposal or further handling as desired.

The hot product stream is withdrawn from the top of the secondary separator (54) through a conduit (58) which feeds the vapor comprising condensable and noncondensable components and some fine residual char and ash to the lower interior space of a baffled condenser (60) where the vapor is immediately quenched. The condenser (60) uses the product liquid as the quench medium.

The condensed liquid product is withdrawn from the bottom of the condenser (60) through a conduit (62) and is fed to a pump (64) which pumps it to a heat exchanger (66) indirectly cooled by water. The cooled product liquid is removed from the heat exchanger (66) and returned by conduit (68) to the top of the condenser (60) as a spray. A conventional transparent vertical sight indicator (61) is mounted on the lower part of the first condenser (60). The sight indicator has high and low liquid level marks. When the volume of liquid in the condenser (60) reaches the high level mark raw pyrolysis liquid is withdrawn through a conduit (63) until the liquid level reaches the low level mark. Liquid is then accumulated in the condenser until it reaches the high level mark again when the raw pyrolysis liquid withdrawal step is repeated.

Noncondensed product vapor is withdrawn from the top of the condenser (60) by conduit (70) and is fed to a packed second condenser column (72) where it is further cooled. Liquid is withdrawn by a conduit (74) from the bottom of the packed second condenser and fed to a pump (76) which pumps it through a water cooled heat exchanger (78). Cooled liquid product is removed from the heat exchanger (78) by conduit (80) and is fed to the top of the packed second condenser (72). The sight indicator has high and low liquid level marks. When the high level mark is reached raw pyrolysis liquid is withdrawn through conduit (75) until the liquid level reaches the low mark.

A vapor stream is removed from the top of the packed second condenser column (72) by a conduit (82) and fed through a water cooled heat exchanger (84) which feeds it to a mist eliminator (88). The vapor is fed from the mist eliminator (88) to a conduit (90) which delivers the vapor to a filter (92). Liquid is removed from the bottom of the filter (92) by means of a conduit (102) and recirculated to the bottom portion of the second condenser column (72) above the level of liquid in the column. A portion of the resulting clean by-product gas stream is ducted from the filter (92) by a conduit (94) to waste while a further portion is taken from the conduit (94) and fed to conduit (96) which feeds into a gas recirculation blower (98). The recirculated gas is fed from the blower (98) to a conduit (100) which feeds into the bottom of the reactor (44).

Suitable feedstocks for producing a high browning, low flavor liquid composition are generally a member of the group consisting of wood, sugars, cellulose, polysaacharides, other cellulosic biomass materials, and/or mixtures thereof. Such feedstocks include a variety of carbohydrate-containing materials including wood, cellulose, sugars or starches. For example, any mono., di., tri. or polysaccharide which contains glucose or glucose monomers many be used. Suitable saccharides include glucose, dextrose, invert sugar, lactose, malt syrup, molasses, starch hydrolysates and fractions therefore, sucrose, cellobiose, hemicellulose and cellulose. Wood also serves as a suitable feedstock although the presence of components in wood, in addition to cellulose, may provide an unduly complex pyrolysis mixture. Other suitable feedstock sources include plant derived material such as seed, leaf and fruit fibers, as well as plant derived syrups and extracts.

After collecting the liquid pyrolysis materials from these feedstocks, it is generally advantageous to add sufficient water to dilute the pyrolysis materials to reduce the ° Brix value of the materials to about 35° Brix or lower, in order to ensure the complete separation of the desired water-soluble components from the undesired water-insoluble components. If the ° Brix value of the diluted pyrolysis solution is greater than about 35° Brix, the separation of benzo(a)pyrene and tars from the aqueous layer may be incomplete.

Furthermore, it is also desirable to ensure that the water-soluble liquid phase of suitable pyrolysis solutions be less than about 35° Brix when subsequent extraction or other treatment steps are performed because these additional steps are less effective at higher ° Brix values, primarily due to the greater solvating effects of the organic components of the more highly concentrated solutions.

Specifically, untreated water-soluble liquid pyrolysis solutions, desirably having a maximum ° Brix value of about 35, may be further improved by additional treatment to lower the amounts of unnecessary organic components in the solution. In one treatment, the liquid solution is extracted with a suitable water-insoluble organic solvent, such as methylene chloride, to remove phenols, flavoring materials, and other food flavoring organic components which provide smoke flavor and aroma, while retaining those organic components which provide browning. Generally, suitable extraction solvents include solvents having a proper range of hydrogen bonding parameters and an appropriate polarity index to solubilize the undesired flavoring organic components present in the water-soluble product. After extraction, the organic solvent is then separated from the aqueous phase to yield a suitable liquid solution which has less flavoring ability.

The water-soluble liquid pyrolysis solution, with or without a prior extraction with methylene chloride or some other suitable organic solvent, may be treated with a nonionic resin, cationic resin or a combination of such resins, to also remove undesired contaminants and flavoring organic components. The resin treatment of liquid solutions produced by slow pyrolysis of wood is described in U.S. Pat. No. 4,959,232 which is incorporated herein by reference. The conditions disclosed therein are suitable for further processing the water-soluble liquid pyrolysis solution obtained from a suitable feedstock with or without a prior organic solvent extraction. The resulting liquid solution has little or substantially no flavoring ability.

After suitable treatment the resulting liquid solution may be diluted with water or concentrated as appropriate depending on the type of application process for which it is to be used.

EXAMPLES

The following examples are presented to further illustrate the invention. In the examples, the concentration values for the organic components in the described liquids are given as ° Brix values or by weight as described above. The ° Brix values were obtained using standard refractory techniques which are well known in the sugar industry. Other typical analytical procedures are described in U.S. Pat. No. 4,876,108.

EXAMPLE 1

'This example compares measurable differences of three liquid compositions, samples A, B and C that are useful in preparing a casing of the invention to a known tar-depleted solution, sample D. The measured differences indicate the suitability of the liquid compositions, A, B, and C, in making an impregnated cellulosic casing according to the invention.

Table 1 lists the analytical data of the liquid composition samples A, B, C and D.

Sample A was prepared from high dextrose corn syrup having 83.7% total solids and 16.3% moisture (62 D.E./44 Baume corn syrup, ADM Corn Sweetners, Cedar Rapids, Iowa) that was heated to about 150° F. and then pumped through steam heated conduits into an upflow circulating fluidized bed reactor described above. The heated corn syrup entered the reactor through a nozzle having a 3/32 inch aperture. The reactor temperature was about 550° C., the vapor residence was about 700 msec, and the pressure was about 1.5 psi. The pyrolysis vapors were condensed and solubilized by direct contact with 20° C. recirculating water to give a liquid product having about 30 ° Brix. The 30 ° Brix solution was extracted with methylene chloride (one volume methylene chloride to ten volumes solution) and then concentrated by evaporation under reduced pressure (−28.3 inches of mercury) at about 50° C. to give a liquid composition of about 45° Brix.

| Sample A had the following composition: | |
|---|---|
| °Brix | 45 |
| Acids | 2.7% |
| Phenols | 2.0 mg/ml |
| Carbonyls | 54.0% |
| Browning Index | 104.0 |
| Transmittance | 82% |
| Viscosity | 4.98 cps |
| Specific Gravity | 1.174 g/m |
| Color | 27.5 |
| Hydroxyacetaldehyde | 16.1% |

Sample B was prepared from powdered cellulose (Avicel pH-101, FMC Corp., Philadelphia, Pa.) that was pyrolyzed in a downflow transport reactor at 550° C. using an inert solid heat carrier. The vapor residence time was about 200 milliseconds and the vapors were condensed directly onto a cold water condenser. The raw pyrolysis liquid was found to be about 70 ° Brix. About 4.2 kilograms of raw liquid were then added to about twenty liters of water and the resulting solution was passed through a column containing ten liters of XAD-4 non-ionic exchange resin (Rohm and Hass Corp., Philadelphia, Pa.). The resin treatment lowered the ° Brix of the solution from 14 to 9. The resin treated solution was then concentrated by evaporation under reduced pressure (−29 inches of mercury) to about 45 ° Brix at 50° C. Sample B was found to have the following composition:

| °Brix | 45 |
|---|---|
| Acids | 2.9% |
| Phenols | 7.3 mg/ml |
| Carbonyls | 22% |
| Browning Index | 44.0 |
| Transmittance | 94% |
| Viscosity | 5.7 cps |
| Specific Gravity | 1.191 g/ml |
| Color | 3.0 |
| Hydroxyacetaldehyde | 10.2% |

Sample C was prepared from about 1640 g of the high dextrose corn syrup liquid composition as described above as sample A which was added to about 2360 g of a 40% aqueous solution of hydroxyacetaldehyde to give a combined mixture, sample C.

The 40% aqueous solution making up part of sample C was prepared by adding water to about 800 g of solid hydroxyacetaldehyde (Red Arrow Products Company Inc., Manitowoc, Wis.) to give a final volume of about 2000 ml. After dissolution of the solids, the solution was filtered. The composition of this 40% solution was:

| °Brix | 28 |
|---|---|
| Acids | <0.2% |
| Browning Index | 94 |
| Hydroxyacetaldehyde | 39.5% |

The combined mixture sample C was found to have the following composition:

| °Brix | 35 |
|---|---|
| Acids | 2.0% |
| Phenols | — |
| Carbonyls | 45.1% |
| Browning Index | 96.5 |
| Transmittance | — |
| Viscosity | 4.36 cps |
| Specific Gravity | 1.1326 g/ml |
| Color | — |

-continued

| | |
|---|---|
| Hydroxyacetaldehyde | 28.4% | for comparative purposes a tar-depleted liquid solution sample D, was prepared according to the description provided in U.S. Pat. No. 4,717,576. Accordingly, a conventional liquid smoke CHARSOL C-10 (Red Arrow Products Company Inc., Manitowoc, Wis.) having a °Brix value of 24, acids value of 11%, phenols value of 16 mg/ml, carbonyls value of 12%, and browning index of 11 was extracted with three portions of methylene chloride equal to about ⅓ the total liquid smoke volume. The tar-depleted liquid smoke was then concentrated by evaporation under a vacuum (−29 inches of mercury) at 50° C. to 45° Brix. Sample D was found to have the following composition:

| | |
|---|---|
| °Brix | 45 |
| Acids | 18.7% |
| Phenols | 8.6 mg/ml |
| Carbonyls | 22.8% |
| Browning Index | 27.5 |
| Transmittance | 67 |
| Viscosity | 5.7 |
| Specific Gravity | 1.120 g/ml |
| Color | 14.0 |
| Hydroxyacetaldehyde | 5.2% |

TABLE 1

| COMPOSITION | °BRIX | BI | VISC | CAR | ACID | PHEN | BI/°BRIX | BI/CAR | BI/ACID | BI/PHEN |
|---|---|---|---|---|---|---|---|---|---|---|
| A | 45 | 104 | 4.98 | 54.0 | 2.7 | 2.0 | 2.31 | 1.9 | 38.5 | 52.0 |
| B | 45 | 44 | 5.7 | 22.0 | 2.9 | 7.3 | 0.98 | 2.0 | 15.2 | 6.0 |
| C | 35 | 96.5 | 4.4 | 45.1 | 2.0 | — | 2.76 | 2.1 | 48.2 | — |
| D | 45 | 27.5 | 5.7 | 22.8 | 18.7 | 8.6 | 0.61 | 1.2 | 1.5 | 3.2 |

BI - browning index
VISC - viscosity (cps)
CAR - carbonyls (wt. %)
ACID - acids (wt. %)
PHEN - phenols (mg/ml)

Two of the sample compositions A and C, have much higher browning capabilities when compared to sample D, as illustrated by the high browning index to °Brix ratio compared to the low browning index to °Brix ratio of sample D.

Advantageously, samples A, B and C have very low levels of acids and substantially higher browning index values. These characteristics are preferred because acids may cause substantial degradation of the cellulosic casings when applied to nonfibrous reinforced cellulosic casings. It should also be noted that samples A, B and C have high browning index to carbonyl ratios compared to sample D which indicates that samples A, B and C have higher browning capabilities even if the amount of carbonyls is the same.

Further, the high values for the ratio BI/PHEN indicate that samples A, B and C give a casing that does not impart an undesirable flavor.

EXAMPLE 2

In this example, two compositions useful to practice the present invention, samples A and B of Example 1, were first diluted and then partially neutralized by addition of sufficient amounts of solid sodium hydroxide to give samples designated A35, A35 N, B35 and B35-N, respectfully. Aliquots of sample A (500 g, 4.98 cps, browning index 104) and sample B (500 g, 5.7 cps, browning index 44) from Example 1 were diluted with enough water to give a final browning index value of about 35 for both aliquots and were labeled as samples A35 and B35. Both diluted samples A35 and B35 were adjusted to a final pH value of about 5 by adding a sufficient amount of solid sodium hydroxide. During the addition of sodium hydroxide the temperature was maintained below 20° C. by a water bath of ice and salt. The pH adjusted samples were labeled A35-N and B35-N. Viscosity values were obtained for the four samples; A35, B35, A35-N and B35-N.

Viscosity values of the two neutralized samples were compared with the viscosity values of two tar-depleted products, G34 and G34-N reported in U.S. Pat. No. 4,717,576. Samples G34 and G34-N have nearly equal reported values of browning index when compared to samples A35 and B35.

Table 2 shows browning index and viscosity for the diluted, neutralized compositions of the invention and known liquid smoke solutions. Large differences in viscosity are evident.

TABLE 2

| Product | pH | Browning Index | Viscosity* |
|---|---|---|---|
| A35 | 3.0 | 35 | 1.3 |
| A35-N | 5 | 35 | 1.5 |
| B35 | 2.9 | 35 | 3.3 |
| B35-N | 5 | 34 | 3.7 |
| G34 | 2** | 34** | 95** |
| G34-N | 5** | 34*** | 197.5** |

*Values as cps at 25° C.
**Values from U.S. Pat. No. 4,717,576.
***Values derived from U.S. Pat. No. 4,717,576.

Known tar-depleted, concentrated, high acid content liquid smoke solutions exhibit a higher viscosity value after neutralization because of the presence of excessive amounts of alkaline salts of organic acids in the solutions. The high acid content of concentrated tar-depleted solutions prevents neutralizing those solutions to useful pH values and still retain acceptable viscosity values. For the liquid compositions, A35 and B35, no noticeable increment in viscosity was found after neutralization due to their low initial acid content. Thus, it is now possible to neutralize compositions having high browning index values without imparting undesirable high viscosity values to those compositions.

Additional analytical data for neutralized liquid compositions useful to practice the invention are listed in Table 2A. To obtain the compositions listed in Table 2A enough base solution (50% sodium hydroxide) was added to the four samples of Example 1, samples A, B, C and D, to give a final pH value of 5.5. During neutralization the temperature was maintained below 20° C. After base treatment, the neutralized samples were adjusted to 35° Brix by diluting with an appropriate amount of water. These samples were designated A35-N, B35-N, C35-N and D35-N and the properties of these samples are listed in Table 2A.

TABLE 2A

| COMP | °BRIX | BI | % CAR | ACID | BI/°BRIX | PHEN* | BI/CAR | BI/AC | BI/PH |
| --- | --- | --- | --- | --- | --- | --- | --- | --- | --- |
| A35-N | 35 | 85.6 | 43.4 | 2.2 | 2.45 | 1.07 | 2.0 | 38.9 | 80.0 |
| B35-N | 35 | 32 | 15.4 | 2.4 | 0.91 | 3.62 | 2.1 | 13.3 | 8.8 |
| C35-N | 35 | 93.1 | 33.7 | 2.0 | 2.66 | 0.59 | 2.8 | 46.6 | 158.0 |
| D35-N | 35 | 16.5 | 12.5 | 12.5 | 0.47 | 4.34 | 1.3 | 1.3 | 3.8 |

BI - browning index
*PHEN - phenols (mg/ml)
CAR - carbonyls (wt. %)
ACID - acids (wt. %)

EXAMPLE 3

Four nonfibrous frankfurter size gel stock cellulosic casings (1–4) were treated with four liquid compositions (A35-N, B35-N, C35-N and D35-N prepared in Example 2 having pH values of about 5.5) by applying these compositions to the external surface of the casings. The casings were passed through a tank containing each of the liquid compositions. The time of contact was regulated in order to control the amount of liquid composition absorbed into the casing. After dipping and doctoring off excess solution, the casings were dried and rehumidified to a water content of about 12 wt%.

The four casings prepared were analyzed and the results are listed in Table 3.

TABLE 3

| Casing | Liquid Composition | Browning Index | Organics Load | Liquid Load | BID |
| --- | --- | --- | --- | --- | --- |
| 1 | A35-N | 85.6 | 0.65 | 1.62 | 0.139 |
| 2 | B35-N | 32 | 0.62 | 1.68 | 0.054 |
| 3 | C35-N | 93.1 | 0.63 | 1.50 | 0.140 |
| 4 | D35-N | 16.5 | 0.64 | 1.75 | 0.029 |

Organics Load mg/cm$^2$
Liquid Load mg/cm$^2$

The results clearly illustrate that cellulosic casings treated with compositions A35-N, B35-N and C35-N of this invention have much higher values of BID than the casing prepared using the solution, D35-N, where all of the casings are loaded with essentially the same amounts of organic components.

EXAMPLE 4

This example shows additional advantages in casings treated with liquid compositions of the invention compared to casings treated with prior art liquid smoke solutions. A series of cellulose casings (5–8) were prepared using the liquid compositions A35-N, B35-N, C35-N and D35-N, prepared in Example 2 to give casing samples 5, 6, 7 and 8, respectively. The method of application was essentially similar to the method described in the Example 3 except that the time of contact of the liquid composition with the casings was regulated for each sample in order to get casings having essentially equal final BID values. Analytical data for the casings are listed in Table 4.

These data illustrate that cellulosic casings of the invention, casings 5–7, do not need to be loaded with excessive amounts of organic components to impart very good browning properties to the casings. The data also indicate that only about one-quarter to one-half of the load of organic components is needed to give approximately equal Browning Index Density values to the casings of the invention compared to casings treated with a known solution such as D35-N. This result is highly desirable because small casing loads do not detrimentally affect the physical properties of cellulose or cellulosic casings, but excessive loads may be detrimental. This advantage is believed to be related to two factors: the low amount of total acids; and the presence of more efficient browning carbonyls which are incorporated into the casing from the liquid compositions A35-N, B35-N and C35-N. This qualitative difference in the type of carbonyls of the exemplified liquid compositions provides the same or higher values of BID using lesser amounts of these compositions.

Another advantage shown in this example is that the casings of this invention have an extremely high ratio of BID to phenols. Casings produced by this invention are very desirable when compared to casings treated with known liquid smoke solution because sausages prepared using casings treated with known liquid smoke solutions often have an undesired strong smoke flavor because of the high content of phenols in the casings.

TABLE 4

| Casing | BID | CELLULOSE | CAR | ACID | PHENOLS | ORG | CAR/BID | PHEN/BID | ORG/BID | CAR/CEL | ACIDS/CEL | PHEN/CEL | ORG/CEL |
| --- | --- | --- | --- | --- | --- | --- | --- | --- | --- | --- | --- | --- | --- |
| 5 (A35-N) | 0.080 | 2.88 | 0.22 | 0.020 | 0.0008 | 0.37 | 2.8 | 0.01 | 4.6 | 0.08 | 0.007 | 0.0003 | 0.13 |
| 6 (B35-N) | 0.072 | 2.91 | 0.25 | 0.053 | 0.0034 | 0.83 | 3.5 | 0.05 | 11.5 | 0.09 | 0.018 | 0.0012 | 0.29 |
| 7 (C35-N) | 0.077 | 2.83 | 0.22 | 0.016 | 0.0008 | 0.35 | 2.9 | 0.01 | 4.5 | 0.08 | 0.006 | 0.0003 | 0.12 |
| 8 (D35-N) | 0.072 | 2.98 | 0.52 | 0.550 | 0.0093 | 1.59 | 7.2 | 0.13 | 22.1 | 0.17 | 0.185 | 0.0031 | 0.53 |

Cellulose (mg/cm$^2$)
ACID - acids (mg/cm$^2$)
BID - browning index density
CAR - carbonyls (mg/cm$^2$)
ORG - organics (mg/cm$^2$)
PHEN - phenols (mg/cm$^2$)

EXAMPLE 5

Sausages were produced with a casing of this invention or with a casing produced with another method. The sausages were prepared with the casings 1, 2, 3 and 4 produced in Example 3. After the casings are dried, rehumidified and shirred, the four different casings were stuffed with a meat smulsion made using the formulation shown in Table 5.

TABLE 5

| INGREDIENTS | % (WEIGHT) |
| --- | --- |
| Pork jowl | 41 |
| Beef shoulder | 40 |
| Sodium Nitrite and Nitrate | 0.024 |

TABLE 5-continued

| INGREDIENTS | % (WEIGHT) |
| --- | --- |
| Salt | 1.9 |
| Spices | 0.5 |
| Water and Ice | 16.6 |

The casings were stuffed using conventional processes but without using a conventional smoking step. During the process, organic components transferred from the casing to the surface of the encased meat emulsion and these organic components reacted with proteins of the emulsion to develop a desired brown smoked color. After chilling the sausages, the casings were removed and the colorimetric parameters "L" (lighter color) and "a" (redder color) were determined for the resulting sausages using a DR. LANGE MICROCOLOR TRISTIMULUS colorimeter standardized with a white plate. For each of the different casings, 15 sausages were tested. Four colorimetric determinations were done on each sausage. A nonimpregnated cellulosic casing stuffed with the same meat emulsion and processed the same way was used as a control. The resulting data are listed in Table 5A.

TABLE 5A

| Casing | L | L-L (control) | a | a-a (control) |
| --- | --- | --- | --- | --- |
| 1 | 48.7 | −9.9 | 19.0 | 6.1 |
| 2 | 54.7 | −3.9 | 15.2 | 2.3 |
| 3 | 48.5 | −10.1 | 18.5 | 5.6 |
| 4 | 57.4 | −1.2 | 13.6 | 0.7 |
| Control | 58.6 | — | 12.9 | — |

The data listed in Table 5A illustrate the advantages of this invention. Sausages prepared using casings of this invention (casings 1, 2 and 3) develop a very good brown color. Sausages prepared as described in the prior art (casing 4), although loaded with approximately the same amount of organics as included in the other casings, did not develop enough brown smoked color required to give an acceptable product.

EXAMPLE 6

It has been found that shirred nonfibrous cellulosic casings treated with a known liquid smoke solution prepared as reported in U.S. Pat. No. 4,511,613 develop dark surface discolorations on the treated casing over time. The dark discolorations are appropriately called "black spots". These black spots represent a weakened area in the casing which is more susceptible to pinholing under stress as well as breakage during stuffing. It has been found that the areas of the black spots are contaminated with high levels of iron compared to the other areas of the casing. Casing deterioration may be experienced in a variety of stages from no visible damage to blister separation to actual holes at the site of these black spots. In addition, it has been observed that the black spots on the casing occasionally transfer to a food contained in the casing which adversely affects the aesthetic quality of the food.

Various attempts have been made to prevent black spot formation when treating casings with liquid smoke solutions. Attempts have included careful processing conditions using cleaning devices for the various machinery process steps and solution cleaning using submicron filtration. These attempts to avoid or minimize iron contamination provide some improvement in reducing black spot formation during storage of liquid smoke treated casings, but they have not provided completely satisfactory results or eliminated black spot formation. Thus, there is a continuing need for a process and/or a composition to prevent the formation of black spots on liquid smoke treated food casings.

To determine the propensity of cellulosic casings made by the invention for developing black spots, lengths of shirred casings were examined for the appearance of any discoloration after impregnation with the liquid composition of the invention compared to a known liquid smoke solution prepared as described in U.S. Pat. No. 4,717,576. Gel stock casings were passed through a tank containing each of the above solutions for a time period sufficient to provide adequate absorption of the solution into the casing. After dipping and doctoring off any excess solution, the impregnated casings were dried, rehumidified, rolled and shirred in a conventional shirring machine. Afterwards, five lengths of each of the impregnated casings were checked for black spots. The resulting data are listed in Table 6.

TABLE 6

| Casing | Liquid Comp. | Load (mg/cm$^2$) | BID | Spots (average number/100 m of casing) |
| --- | --- | --- | --- | --- |
| I | A35-N | 1.61 | 0.138 | 0 |
| II | D35-N | 2.66 | 0.044 | 35 |

This example establishes that casings impregnated with a liquid composition according to the invention do not develop black spots, thus avoiding the likelihood of breaking during stuffing and the staining of a food contained in the casing.

I claim:

1. A peelable casing made by a method comprising the step of:
   contacting the casing with a high browning, low flavor liquid composition having soluble organic components and a ratio of browning index to °Brix greater than 0.9, wherein the liquid composition is derived from a feedstock selected from the group consisting of a sugar, a starch, a monosaccharide, a disaccharide, a trisaccharide, a starch hydrolysate, cellobiose, hemi-cellulose and mixtures thereof, and wherein the composition imparts a satisfactory brown color to a food subsequently encased in the casing without adding undesired sensory properties to the food.

2. A casing according to claim 1 wherein the ratio of browning index to °Brix of the liquid composition is greater than 1.5.

3. A casing according to claim 1 wherein the organic components of the liquid composition comprise acids, carbonyls, phenolls, and salts thereof.

4. A casing according to claim 3 wherein the liquid composition has a ratio of browning index to acids greater than 5.0, a ratio of browning index to carbonyls greater than 1.8, and a ratio of browning index to phenols greater than 8.5.

5. A casing according to claim 3, wherein the liquid composition has a ratio of browning index to acids greater than 12.0, a ratio of browning index to carbonyls equal to or greater than 2.0, and a ratio of browning index to phenols greater than 30.0.

6. A casing according to claim 1 wherein the casing is selected from the group consisting of nonreinforced cellulosic casings and fibrous reinforced cellulosic casings.

7. A casing according to claim 1 wherein the casing is a nonreinforced cellulosic casing.

8. A casing according to claim 1 wherein the viscosity of the liquid composition is less than 300 cps.

9. A casing according to claim 1 wherein the viscosity of the liquid composition is less than 90 cps.

10. A casing according to claim 1 wherein the viscosity of the liquid composition is less than 10 cps.

11. A casing according to claim 1 wherein the liquid composition has a pH value of about 5.5.

12. A casing according to claim 1 wherein the liquid composition is derived from the group consisting of sugars, starches and mixtures thereof.

13. A casing according to claim 1 further comprising the step of shirring the casing.

14. A peelable cellulosic casing treated with a high browning, low flavor liquid composition, wherein the liquid composition includes soluble organic components and has a ratio of browning index to ° Brix greater than 0.9 and is derived from a feedstock selected from the group consisting of a sugar, a starch, a monosaccharide, a disacchardie, a trisaccharide, a starch hydrolysate, cellobiose, hemi-cellulose and mixtures thereof, and wherein the treated casing has a ratio of organic components to browning index density less than 12.0.

15. A casing according to claim 14 wherein the ratio of organic components to browning index density is less than 5.0.

16. A casing according to claim 14 wherein the casing is selected from the group consisting of nonreinforced cellulosic casings and fibrous reinforced cellulosic casings.

17. A casing according to claim 14 wherein the casing is a nonreinforced cellulosic casing.

18. A peelable cellulosic casing treated with a high browning, low flavor liquid composition, wherein the liquid composition includes soluble organic components and has a ratio of browning index to ° Brix greater than 0.9 and is derived from a feedstock selected from the group consisting of a sugar, a starch, a monosaccharide, a disacchardie, a trisaccharide, a starch hydrolysate, cellobiose, hemi-cellulose and mixtures thereof, and wherein the treated casing has a ratio of phenols to browning index density less than 0.1.

19. A casing according to claim 18 wherein the casing is selected from the group consisting of nonreinforced cellulosic casings and fibrous reinforced cellulosic casings.

20. A casing according to claim 18 wherein the casing is a nonreinforced cellulosic casing.

21. A food product produced by a process comprising the steps of:
(a) treating a peelable casing with a high browning, a low flavor liquid composition having soluble organic components and a ratio of browning index to ° Brix greater than 0.9 to provide a treated peelable casing, wherein the liquid composition is derived from a feedstock selected from the group consisting of a sugar, a starch, a monosaccharide, a disaccharide, a trisaccharide, a starch hydrolysate, cellobiose, hemicellulose, and mixtures thereof;
(b) introducing a food substance into the treated peelable casing to provide an encased food product;
(c) heating the encased food product such that the treated peelable casing imparts a satisfactory brown color to the food without adding undesired sensory properties to the food; and
(d) removing the treated peelable casing from the encased food product.

* * * * *

UNITED STATES PATENT AND TRADEMARK OFFICE
CERTIFICATE OF CORRECTION

PATENT NO. : 5,270,067          Page 1 of 2
DATED      : December 14, 1993
INVENTOR(S) : Underwood et al.

It is certified that error appears in the above-indentified patent and that said Letters Patent is hereby corrected as shown below:

Col. 2, line 67, "becomes to" should be --becomes too--.

Col. 3, line 2, "tar.depleted" should be --tar-depleted-.

Col. 4, lines 28-29, "(GLYCOL)(CELLULOSE)" should be --(GLYCOL)-(CELLULOSE)--.

Col. 6, line 34, "smoke.like" should be --smoke-like--.

Col. 6, line 62, "polysaacharides" should be --polysaccharides--.

Col. 6, line 65, "gird" should be --grid--.

Col. 8, line 24, "polysaacharides" should be --polysaccharides--.

Col. 8, line 28, "mono., di., tri." should be --mono-, di-, tri- --.

Col. 10, line 22, "Rohm and Hass" should be --Rohm and Haas--.

Col. 10, line 58, "mixture sample C" should be "mixture, sample C--.

Col. 11, line 5, "for comparative" should be --For comparative--.

Col. 11, line 64, "A35N" should be --A35-N--.

Col. 16, line 18, "machine, Afterwards" should be --machine. Afterwards--

Col. 16, line 55, "phenolls" should be --phenols--.

Col. 17, line 24, "disacchardie" should be --disaccharide--.

UNITED STATES PATENT AND TRADEMARK OFFICE
CERTIFICATE OF CORRECTION

PATENT NO.  : 5,270,067
DATED       : December 14, 1993
INVENTOR(S) : Underwood, et al It is certified that error appears in the above-indentified patent and that said Letters Patent is hereby corrected as shown below:

Col. 18, line 7, "disacchardie" should be --disaccharide--

Signed and Sealed this

Fourteenth Day of June, 1994

Attest:

BRUCE LEHMAN

Attesting Officer

Commissioner of Patents and Trademarks